United States Patent [19]

Granatek et al.

[11] 4,001,409
[45] Jan. 4, 1977

[54] INJECTABLE FORMULATIONS OF 7-[D-α-AMINO-α-(P-HYDROXYPHENYL)ACETAMIDO]-3-(1,2,3-TRIAZOL-5-YLTHIOMETHYL)-3-CEPHEM-4-CARBOXYLIC ACID

[75] Inventors: Alphonse Peter Granatek, Baldwinsville; Murray Arthur Kaplan, Syracuse, both of N.Y.

[73] Assignee: Bristol-Myers Company, New York, N.Y.

[22] Filed: May 23, 1975

[21] Appl. No.: 580,268

[52] U.S. Cl. .............................................. 424/246
[51] Int. Cl.$^2$ ........................................ A61K 31/54
[58] Field of Search ........................... 424/114, 246

[56] References Cited
UNITED STATES PATENTS 3,855,213  12/1974  Dunn et al. ................... 260/243 C
3,867,380  2/1975  Dunn et al. ......................... 424/246

OTHER PUBLICATIONS
Proskouriakoff, Jacs., vol. 55, pp. 2132–2134, (1933).

*Primary Examiner*—Albert T. Meyers
*Assistant Examiner*—Daren M. Stephens
*Attorney, Agent, or Firm*—David M. Morse

[57] ABSTRACT

Antibacterial compositions comprising 7-[D-α-amino-α-(p-hydroxyphenyl)acetamido]-3-(1,2,3-triazol-5-ylthiomethyl)-3-cephem-4-carboxylic acid in the form of a hydrate or a hydrochloride salt and a sodium, potassium or calcium salt of levulinic acid have been found to be stable, useful, water-soluble forms of the cephalosporin antibiotic especially advantageous for parenteral administration.

21 Claims, No Drawings

INJECTABLE FORMULATIONS OF 7-[D-α-AMINO-α-(p-HYDROXYPHENYL)-)ACETAMIDO]-3-(1,2,3-TRIAZOL-5-YLTHIOMETHYL)-3-CEPHEM-4-CARBOXYLIC ACID

BACKGROUND OF THE INVENTION

1. Field of the Invention

The novel and useful formulations of the antibiotic 7-[D-α-amino-α-(p-hydroxyphenyl)acetamido]-3-(1,2,3-triazol-5-ylthiomethyl)-3-cephem-4-carboxylic acid provided by the present invention possess in general the usual attributes of the cephalosporin family of antibacterial agents and are particularly useful in the treatment of bacterial infections by injection.

2. Description of the Prior Art

The preparation of the compound 7-[D-α-amino-α-(p-hydroxyphenyl)acetamido]-3-(1,2,3-triazol-5-ylthiomethyl)-3-cephem-4-carboxylic acid having the formula

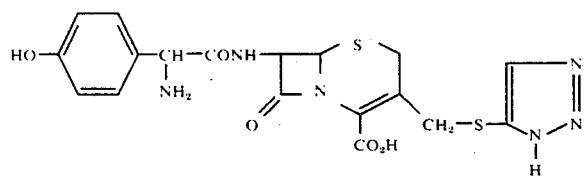

I has been described in German published application No. 2,364,192 (corresponding to U.S. application Ser. No. 318,340 filed Dec. 26, 1972) and also in U.S. Pat. No. 3,867,380 which issued Feb. 18, 1975. The compound is therapeutically effective against infections caused by both Gram-positive and Gram-negative organisms, and it may be administered both orally and parenterally.

The known pharmaceutical forms of the compound of formula I, including the zwitterion free acid form disclosed in the above-mentioned U.S. Ser. No. 318,340, the zwitterion 1,2- propylene glycolate disclosed in U.S. application Ser. No. 431,251 filed Jan. 7, 1974 and the zwitterion hydrate forms disclosed in U.S. application Ser. No. 473,039 filed May 24, 1974 cannot be administered intravenously because of their relatively low solubility in water.

Attempts to prepare stable, water-soluble salts of compound I which could be employed in providing solutions for injection have not been successful. The alkali metal salts of compound I have sufficient solubility in water to provide true solutions necessary for intravenous administration but, unfortunately, all attempts at preparing these salts, e.g., by reaction of an alkali metal hydroxide with the cephalosporin free acid in an aqueous reaction medium, have resulted in rapid inactivation of the antibiotic. The problem of preparing suitable water-soluble salts of compound I has been especially complicated since in addition to the normal β-lactam instability at higher pH ranges, the triazole moiety at the 3-position of cephalosporin I is found to split off rapidly at alkaline pH, i.e. pH~7.0 or higher, resulting in formation of an inactive or low potency degradation product. An acid addition salt of compound I with hydrochloric acid has also been made (see Preparation of Starting Materials below). While soluble, this salt was found to result in significant venous irritation and muscle damage when administered parenterally in test animals, presumably due to the low pH of the aqueous salt solutions.

It is the object of the present invention to provide 7-[D-α-amino-α-(p-hydroxyphenyl)acetamido]-3-(1,2,3-triazol-5-ylthiomethyl)-3-cephem-4-carboxylic acid in novel pharmaceutically acceptable forms which upon the addition of sterile water or a sterile aqueous vehicle will give true solutions of the cephalosporin antibiotic suitable for parenteral administration.

It is another object of the present invention to provide water-soluble pharmaceutical forms of cephalosporin I which have acceptable thermal stability in the solid state, which upon reconstitution with sterile water or a sterile aqueous vehicle provide true solutions of from about 10 to 350 mg. 7-[D-α-amino-α-(p-hydroxyphenyl)acetamido]-3-(1,2,3-triazol-5-ylthiomethyl)-3-cephem-4-carboxylic acid per ml. of solution having a useful life of at least several hours at room temperature and which show freedom from excessive vein or muscle irritation upon intravenous or intramuscular administration.

It is still another object of the present invention to provide injectable aqueous solutions of compound I which (a) have a pH range of from about 3.5 to 8.0, (b) contain from about 10 to 350 mg. of compound I per ml. of solution, (c) result in freedom from excessive vein or muscle irritation upon intravenous or intramuscular administration and (d) have a useful life of at least several hours at room temperature.

It is a further object of the present invention to provide processes for preparing the water-soluble solid formulations and aqueous solutions mentioned above.

Other objects, aspects and advantages of this invention will become apparent from reading the description which follows.

SUMMARY OF THE INVENTION

The present invention provides novel water-soluble pharmaceutical formulations of the antibiotic 7-[D-α-amino-α-(p-hydroxyphenyl)acetamido]-3-(1,2,3-triazol-5-ylthiomethyl)-3-cephem-4-carboxylic acid which (1) upon addition of sterile water or a sterile aqueous vehicle comprising in solution a sodium, potassium or calcium salt of levulinic acid will give true solutions for parenteral administration, (2) have acceptable thermal stability in the solid state, (3) in aqueous solution have a useful life of at least several hours at room temperature and (4) on intravenous or intramuscular injection result in freedom from excessive muscle or vein irritation.

More particularly, the present invention provides (1) pharmaceutical compositions comprising 7-[D-α-amino-α-(p-hydroxyphenyl)acetamido]-3-(1,2,3-triazol-5-ylthiomethyl)-3-cephem-4-carboxylic acid in the form of a hydrate or hydrochloride salt and a sodium, potassium or calcium salt of levulinic acid, said levulinic acid salt being present in an amount of from about 25 to about 200% of the weight of the cephalosporin hydrate or hydrochloride and (2) stable injectable solutions comprising the above-mentioned cephalosporin hydrate or hydrochloride and sodium, potassium or calcium levulinate in the proportions mentioned in (1) with sufficient sterile water to provide pH 3.5 to 8 solutions containing 7-[D-α-amino-α-(p-hydroxyphenyl)acetamido]-3-(1,2,3-triazol-5-ylthiomethyl)-3-cephem-4-carboxylic acid in concentrations of from about 10 to 350 mg. per ml. of solution.

A preferred embodiment comprises the mixture of one part by weight of 7-[D-α-amino-α-(p-hydroxyphenyl)acetamido]-3-(1,2,3-triazol-5-ylthiomethyl)-3-cephem-4-carboxylic acid hydrate, most preferably the amorphous monohydrate, and about 0.25 to about 2.0 parts by weight of the sodium, potassium or calcium salt of levulinic acid, most preferably sodium levulinate.

The solid mixture may be prepared by intimately admixing a sterile hydrate of 7-[D-α-amino-α-(p-hydroxyphenyl)acetamido]-3-(1,2,3-triazol-5-ylthiomethyl)-3-cephem-4-carboxylic acid and sterile sodium, potassium or calcium levulinate in the proportions recited above. While crystalline hydrates including especially the crystalline sesquihydrate disclosed in U.S. application Ser. No. 473,039 may be used, the preferred hydrate is the amorphous monohydrate because of its greater rate of dissolution upon reconstitution. The proportions of hydrate and levulinate may be varied within the range described to give upon reconstitution true solutions having a pH of about 3.5 to 8. The cephalosporin compound and levulinate are preferably ground to at least 200 mesh so as to maximize the rate of solution upon reconstitution. A preferred embodiment is the mixture of one part by weight of amorphous 7-[D-α-amino-α-(p-hydroxyphenyl)acetamido]-3-(1,2,3-triazol-5-ylthiomethyl)-3-cephem-4-carboxylic acid monohydrate and about 0.75–1.0 parts by weight of sodium levulinate. This mixture upon reconstitution with sterile water will give stable true solutions containing advantageously from about 10 to 350 mg. 7-[D-α-amino-α-(p-hydroxyphenyl)acetamido]-3-(1,2,3-triazol-5-ylthiomethyl)-3-cephem-4-carboxylic acid per ml. of solution and having a pH within the range of about 4.5 to 7.8.

If in the mixture described above the cephalosporin hydrate is replaced with the hydrochloric acid salt of 7-[D-α-amino-α-(p-hydroxyphenyl)acetamido]-3-(1,2,3-triazol-5-ylthiomethyl)-3-cephem-4-carboxylic acid, a solid water-soluble composition is formed which upon reconstitution with sterile water forms true solutions for injection having substantially the same desirable properties resulting from use of the hydrate-levulinate mixture. At elevated temperatures, however, the hydrochloride is found to react with the levulinate, thus substantially limiting the commercial usefulness of the hydrochloride-levulinate solid mixture.

It was surprisingly found according to the present invention that the addition of sodium, potassium or calcium levulinate to 7-[D-α-amino-α-(p-hydroxyphenyl)acetamido]-3-(1,2,3-triazol-5-ylthiomethyl)-3-cephem-4-carboxylic acid hydrate greatly enhances the solubility of the cephalosporin hydrate and allows preparation of relatively high concentration and stable true solutions of this valuable cephalosporin antibiotic. The solid compositions are found to be satisfactorily stable (less than 10% activity loss) for at least one month at 45° C. and the solutions formed upon reconstitution with sterile water exhibit less than a 10% activity loss after storage for 24 hours at room temperature. The pH range of the aqueous solutions is found to result in greatly reduced muscle and vein irritation when compared with solutions of the hydrochloride salt.

The present invention also provides a stable, solid, water-soluble composition suitable upon reconstitution with sterile water as a stable injectable solution of 7-[D-α-amino-α-(p-hydroxyphenyl)acetamido]-3-(1,2,3-triazol-5-ylthiomethyl)-3-cephem-4-carboxylic acid, said composition being prepared by the process comprising 1. forming an aqueous solution of one part by weight of 7-[D-α-amino-α-(p-hydroxyphenyl)acetamido]-3-(1,2,3-triazol-5-ylthiomethyl)-3-cephem-4-carboxylic acid hydrate or hydrochloride and about 0.25 to about 2.0 parts by weight of sodium, potassium or calcium levulinate; and
2. lyophilizing the so-produced aqueous solution to produce the desired solid composition.

The aqueous solution in Step (1) is prepared by adding to sterile water the sterile cephalosporanic acid hydrate or hydrochloride, preferably the amorphous monohydrate or amorphous mono-hydrochloride, and the sterile sodium, potassium or calcium levulinate, most preferably sodium levulinate, in a proportion of one part by weight of cephalosporanic acid compound to form about 0.25 to about 2.0, most preferably about 0.75 to 1.0, parts by weight of the levulinic acid salt. As in the case of the hydrate-levulinate mixture described above, the cephalosporanic acid compound and levulinate are preferably used in a finely divided state, i.e. at least about 200 mesh, so as to increase the rate of solution. The aqueous solution is then sterilely lyophilized to produce the desired solid water-soluble composition.

Also provided by the present invention is a stable, solid, water-soluble composition suitable upon reconstitution with sterile water as an injectable solution of 7-[D-α-amino-α-(p-hydroxyphenyl)acetamido]-3-(1,2,3-triazol-5-ylthiomethyl)-3-cephem-4-carboxylic acid, said composition being prepared by the process comprising 1. forming an aqueous solution of one part by weight of 7-[D-α-amino-α-(p-hydroxyphenyl)acetamido]-3-(1,2,3-triazol-5-ylthiomethyl)-3-cephem-4-carboxylic acid hydrate or hydrochloride and about 0.25 to about 2.0 parts by weight of sodium, potassium or calcium levulinate; and
2. adding the so-produced aqueous solution to a sufficient quantity of ethanol, n-propanol or isopropanol to effect precipitation of the desired solid composition.

Preparation of the aqueous solution in Step (1) including the preferred starting materials, proportions and particle size is performed in the same manner as for the lyophilized composition described above. The solution is then added, preferably with rapid stirring, to a sufficient quantity of a sterile alcohol selected from ethanol, n-propanol or isopropanol, preferably n-propanol, to effect precipitation of the desired solid. Good yields of product are obtained if the aqueous solution is added to about 15 to 20 volumes of the alcohol. Following precipitation the precipitate may be filtered, washed with a suitable organic solvent in which the solid is substantially insoluble, e.g., ethanol, n-propanol, isopropanol or acetone, and then dried, e.g., in a vacuum oven at 56° C. for 24 hours, to give the desired water-soluble solid composition.

The precise nature of the solid compositions prepared above by lyophilization and by alcohol precipatation has not yet been determined. It is believed, however, that the solids are either physical mixtures as in the case of the hydrate-levulinate mixture or else weakly-bound complexes. In any event, both of the solids readily dissociate when reconstituted with water to produce true solutions of cephalosporin I in concentrations up to at least 350 mg./ml. Both of the solid compositions will allow pH 3.5 to 8 solutions to be formed which are stable for at least several hours at room temperature and which upon parenteral administration show freedom from the excessive muscle and venous irritation exhibited by the hydrochloride salt solution.

Attempts to form analogous compositions (physical mixtures, lyophilized solids and alcohol precipitated solids) of cephalosporanic acid I and a sodium, potassium or calcium salt of pyruvic acid, another water-soluble ketoacid, resulted in solid compositions giving upon reconstitution true solutions having substantially the same desirable properties as with the levulinate compositions described above. Surprisingly and unexpectedly, however, the pyruvate solutions when injected into standard laboratory test animals, e.g. rabbits, demonstrated a significantly higher degree of nephrotoxicity than that shown with the levulinate compositions.

In yet another aspect the present invention provides a two-component antibiotic preparation suitable upon mixing of the components as a stable injectable solution of 7-[D-α-amino-α-(p-hydroxyphenyl)acetamido]-3-(1,2,3-triazol-5-ylthiomethyl)-3-cephem-4-carboxylic acid, said preparation comprising sterile 7-[D-α-amino-α-(p-hydroxyphenyl)acetamido]-3-(1,2,3-triazol-5-ylthiomethyl)-3-cephem-4-carboxylic acid, said preparation comprising sterile 7-[D-α-amino-α-(p-hydroxyphenyl)acetamido]-3-(1,2,3-triazol-5-ylthiomethyl)-3-cephem-4-carboxylic acid hydrate or hydrochloride, preferably amorphous monohydrate or amorphous mono-hydrochloride, in combination with a sterile vehicle comprising an aqueous solution of sodium, potassium or calcium levulinate, preferably sodium levulinate, said cephalosporanic acid compound and levulinic acid salt being in proportion of about one part by weight of cephalosporanic acid compound to about 0.25 to about 2.0, most preferably about 0.75 to 1.0, parts by weight of levulinic acid salt. The cephalosporanic acid compound is preferably used in a finely divided state, e.g. 200 mesh, so as to facilitate reconstitution.

The sterile cephalosporin hydrate or hydrochloride is placed in a suitable capped sterile vial and accompanied by a vial containing the sterile aqueous levulinate solution, said solution being most preferably in a concentration of about 20% w/v. When administering the preparation, the physician reconstitutes the vial of cephalosporanic acid hydrate or hydrochloride with the aqueous levulinate vehicle to give a true solution for injection having the same desirable pH, stability and and low muscle and vein irritation properties of solutions prepared from the other solid compositions described above. Solutions having concentrations of cephalosporanic acid I of from about 10 to at least 350 mg./ml. can be prepared from the two component preparation.

The antibiotic solutions prepared according to the present invention exhibit substantially the same potency and spectrum in vivo and in vitro as the 7-[D-α-amino-α-(p-hydroxyphenyl)acetamido]-3-(1,2,3-triazol-5-ylthiomethyl)-3-cephem-4-carboxylic acid zwitterion disclosed in West German OLS 2,364,192.

In the treatment of bacterial infections in mammals, the solutions provided according to the present invention may be administered either orally or parenterally, but preferably parenterally, in an amount which will vary with the nature of the subject under treatment, i.e. species, size and weight of subject and severity of the infection. In humans the solutions may be administered parenterally in an amount of from about .5 to 200 mg./kg./day.

PROCEDURES FOR PREPARATION OF STARTING MATERIALS

A. Purified 7-[D-α-amino-α-(p-hydroxyphenyl)acetamido]-3-(1,2,3-triazol-5-ylthiomethyl)-3-cephem-4-carboxylic acid methanolate 1. One hundred grams of 7-[D-α-amino-α-(p-hydroxyphenyl)acetamido]-3-(1,2,3-triazol-5-ylthiomethyl)-3-cephem-4-carboxylic acid methanolate (as prepared by the method of Example 6 of West German OLS 2,364,192) adduct is rapidly stirred in 300 ml. of water.

2. Eighty grams of levulinic acid (or pyruvic acid) is added.

3. Concentrated hydrochloric acid is slowly added with rapid stirring to pH 0.8–1.2 to obtain a solution or near solution. The solution is cooled to 20°–25° C. if required.

4. Forty percent sodium hydroxide is added over a 5 minute period to the very rapidly stirring solution of Step (3) to a pH of 4.5 (a precipitate may come down at pH 2.0–3.0 and then go into solution at pH 4–4.5). Do not allow the temperature to rise above 27° C.

5. The solution or near solution is cooled to 4°–10° C. and added with very rapid stirring to 500 ml. of 4°–10° C. water. A precipitate forms.

6. The mixture is stirred at 4°–10° C. for 5 minutes. The precipitate which contains most of the color and impurities is removed by filtration. The precipitate is washed with 50 ml. of water, 75 ml. of methanol and vacuum dried at 50° C. for 25 hours. Yield 5–15 grams of tan-brown solids. (0–500 units/mg.)

7. Fifteen grams of activated charcoal (Darco G60 or KB) is added to the filtrate of the precipitate of Step 6. The mixture is stirred at ambient temperature for 0.5 hours.

8. The carbon is removed by filtration and washed with 40 ml. of water. The water wash is added to the filtrate.

9. The filtrate is sterilely filtered through a 0.22 micron Millipore filter. Steps 4–9 should be completed within four hours.

10. An equal volume (approximately 1 liter) of sterile, pyrogen-free methanol is added to the pH 4.5 solution of Step 9 with moderate stirring. Crystals form in about one minute. Maintain pH at 4.5.

11. The mixture is stirred at 18°–23° C. for 1 hour.

12. The brillant white crystals are removed by filtration, washed with 175 ml. of sterile 50% methanol, 300 ml. of sterile methanol and vacuum dried at 56° C. for 24 hours. Yield: 65–75 grams (bio yield; 70–80%)

B. Purified 7-[D-α-amino-α-(p-hydroxyphenyl)acetamido]-3-(1,2,3-triazol-5-ylthiomethyl)-3-cephem-4-carboxylic acid 1,2-propylene glycolate 1. One hundred grams of 7-[D-α-amino-α-(p-hydroxyphenyl)acetamido]-3-(1,2,3-triazol-5-ylthiomethyl)-3-cephem-4-carboxylic acid methanolate (as prepared by the method of Example 6 of West German OLS 2,364,192) is rapidly stirred in 300 ml. of water.

2. Eighty grams of levulinic acid (or pyruvic acid) is added.

3. Concentrated hydrochloric acid is slowly added with added with rapid stirring to pH 0.8–1.2 to obtain a solution or near solution. The solution is cooled to 20°–25° C. if required.

4. Forty percent sodium hydroxide is added over a 5 minute period to the very rapidly stirring solution of Step (3) to a pH of 4.5 (a precipitate may come down at pH 2.0–3.0 and then go into solution at pH 4–4.5). Do not allow the temperature to rise above 27° C.

5. The solution or near solution is cooled to 4°–10° C. and added with very rapid stirring to 500 ml. of 4°–10° C. water. A precipitate forms.

6. The mixture is stirred at 5°–10° C. for 5 minutes. The precipitate which contains most of the color and impurities is removed by filtration. The precipitate is washed with 50 ml. of water, 75 ml. of methanol and vacuum dried at 50° C. for 25 hours. Yield 5–15 grams of tan-brown solids. (0–500 units/mg.)

7. Fifteen grams of activated charcoal (Darco G60 or KB) is added to the filtrate of the precipitate of Step 6. The mixture is stirred at ambient temperature for 0.5 hours.

8. The carbon is removed by filtration and washed with 40 ml. of water. The water wash is added to the filtrate.

9. The filtrate is sterilely filtered through a 0.22 micron Millipore filter. Steps 4–9 should be completed within four hours.

10. An equal volume (approximately 1 liter) of sterile, pyrogen free 1,2-propylene glycol is added to the pH 4.5 solution of Step 9 with moderate stirring. Crystals from in about one minute. Maintain pH at 4.5.

11. The mixture is stirred at 18°–23° C. for 1 hour.

12. The brillant white crystals are removed by filtration, washed with 175 ml. of sterile 50% propylene glycol water, 450 ml. of sterile methanol and vacuum dried at 56° C. for 24 hours.

13. Yield 70–80 grams (bio yield 75–85% of the title product (bioassay 880–890 units/mg.

C.

7-[D-α-amino-α-(p-hydroxyphenyl)acetamido]-3-(1,2,3-triazol-5-ylthiomethyl)-3-cephem-4-carboxylic acid amorphous monohydrate 1. Purified 7-[D-α-amino-α-(p-hydroxyphenyl)acetamido]-3-(1,2,3-triazol-5-ylthiomethyl)-3-cephem-4-carboxylic acid methanolate is prepared as described in Procedure A.

2. Ten grams of the purified methanolate is added with very rapid stirring over a 5 minute period to 20 ml. of 30°–40° C. water containing 10 grams of levulinic acid. A pH 3.5–3.9 suspension is obtained. The mixture is slurried for 15 minutes at ambient temperature.

3. The crystals are removed by filtration and washed with 5 ml. of water. The water wash is added to the filtrate (this is filtrate A). The crystals are washed with 35 ml. of methanol and vacuum dried at 50° C. for 24 hours. Yield: 1.5–2.0 grams. These crystals are saved and may be used again as described in Step 2.

4. Filtrate A is sterilely filtered by suitable procedures to remove pyrogens bacteria and particles. This step should be completed within 4 hours.

5. The solution is added over a 5 minute interval to 400–500 ml. of very rapidly stirring, sterile, pyrogen-free acetone. An amorphous precipitate forms.

6. The mixture is slurried for 10 minutes.

7. The solids are removed by filtration, washed with 100 ml. of sterile acetone and vacuum dried at 50°–56° C. for 24 hours. Yield: approximately 7–8 grams of title product.

PROPERTIES OF AMORPHOUS MONOHYDRATE a. % water, KF = 2.5–4.5
b. NMR: approximately 0.1–0.2 moles of adsorbed acetone, trace of levulinate
c. Bio-assay: 900–935 units/mg.

D.

7[D-α-amino-α-(p-hydroxyphenyl)acetamido]-3-(1,2,3-triazol-5-ylthiomethyl)-3-cephem-4-carboxylic acid amorphous mono-hydrochloride 1a. Ten grams of the purified methanolate of Procedure A is suspended in 50 ml. of methanol. The mixture is rapidly stirred at 20°–24° C. and 1.72 ml. of concentrated hydrochloric acid is added over a 3 minute period. A solution or near solution is obtained.

1b. Ten grams of the purified 1,2-propylene glycolate of Procedure B is suspended in 50 ml. of methanol. The mixture is rapidly stirred at 20°–24° C. and 1.6 ml. of concentrated hydrochloric acid is added over a 3 minute period. A solution or near solution is obtained.

2. To the solution of 1a or 1b above, 2.0 grams of activated charcoal (Darco G60) is added and the mixture is slurried for 0.5 hour. The carbon is removed by filtration and washed with 20 ml. of methanol. The methanol wash is added to the filtrate.

3. Pass the combined filtrate and wash of Step 2 through a sterile 0.22 micron Millipore filter into an appropriate sterile container or tank located in a sterile area. Steps 2 and 3 should be completed within 4 hours.

4. In a sterile area using aseptic technique, the sterile filtered solution of Step 3 is added over a 10 minute period with very rapid stirring to 750 to 1000 ml. of dry sterile 0.22 micron Millipore filtered ethyl acetate. An amorphous precipitate forms. The mixture is slurried for 10 minutes.

5. Maintaining aseptic technique and using sterile equipment, remove the precipitate by filtration.

6. Wash the filter cake with 150 ml. of sterile 0.22 micron millipore filtered ethyl acetate. Vacuum dry the filter cake at 55°–60° C. for 48 hours. Yield: 9–9.5 grams.

| PROPERTIES OF AMORPHOUS MONO-HYDROCHLORIDE | | | |
|---|---|---|---|
| a. | Bio-assay = 820–850 mcg./mg. | | |
| b. | % H₂O, KF = 1.5–3.0 | | |
| c. | % Cl = 6.5–8.0 | | |
| d. | % Ethyl acetate = 0.2–0.3 mole (4–5%) | | |
| e. | IR-NMR = Consistent for a mono-hydrochloride, no methanol or propylene glycol present. Approximately 0.2–0.3 moles of ethyl acetate present. The 3-triazole is 100% intact | | |
| f. | Heat stability = | 100° C., 24 hours = | 7–14% loss |
| | | 100° C., 48 hours = | 10–15% loss |
| | | 56° C., 4 weeks = | 1–6% loss |

D$_a$. Alternate Procedure for preparation of amorphous mono-hydrochloride

1. Ten grams of the purified methanolate from Procedure A is added to 75–100 ml. of rapidly stirring isopropanol at 20°–24° C.

2. One and 0.72 ml. of concentrated hydrochloric acid is added over a 5 minute period. A solution or near solution is obtained in about 15 minutes of rapid stirring.

3. Two grams of activated charcoal (Darco-G60) is added and the mixture is slurried for 0.5 hour. The carbon is removed by filtration and washed with 20 ml. of isopropanol which is added to the filtrate.

4. The combined filtrate and wash is azeotropically concentrated (heating bath no higher than 40° C) at high vacuum until approximately 40–50% of the isopropanol has been removed (solution should be dry).

5. The isopropanol solution of Step 4 (at 20°–24° C.) is passed through a sterile 0.22 micron Millipore filter into an appropriate sterile container or tank located in a sterile area.

6. Add the sterile isopropanol solution of Step 5 into 10–15 volumes of rapidly stirring sterile, DRY chloroform over a 5 minute period. An amorphous precipitate forms. The mixture is slurried for 5–10 minutes.

7. The curd-like suspension is passed through a sterile 60–100 mesh screen (or sterilely milled to 60–100 mesh).

8. The mixture is sterilely filtered. The filter-cake tends to crack and channel and requires tamping to pack. The filter cake is washed with 30 ml. of sterile, dry chloroform and sterilely dried at 50°–60° C. for 24 hours.

PROPERTIES OF AMORPHOUS MONO-HYDROCHLORIDE a. Bio-assay = 900 mcg./mg.
b. % $H_2O$, KF = 3.7–5.5
c. % Chlorine = 6.8–7.4
d. Solvents = Substantially solvent-free
e. IR-NMR = Consistent for structure, triazole moiety intact
f. Stability = Less than 10% loss for 1 month at 56° C.

$D_b$. Alternate Procedure for preparation of amorphous mono-hydrochloride

1. Ten grams of the purified methanolate from Procedure A is added to 30–50 ml. of deionized water at 20°–24° C.

2. The mixture is rapidly stirred at 20°–24° C. and 1.72 ml. of concentrated hydrochloric acid is added over a 2–3 minute period. A pH 1.2–1.6 solution or near solution is obtained.

3. Two grams of activated charcoal (Darco G-60) is added and the mixture is slurried for 0.5 hour. The carbon is removed by filtration and washed with 20 ml. of deionized water. The water wash is added to the filtrate.

4. Pass the combined filtrate and wash of Step 3 through a sterile 0.22 micron Millipore filter into an appropriate sterile container or tank located in a sterile area.

5. The sterile solution is sterilely lyophilized, in-vial or as a bulk.

PROPERTIES OF AMORPHOUS MONO-HYDROCLHORIDE a. Bio-assay = 900 mcg./mg.
b. % $H_2O$, KF = 3.7–5.5
c. % Chlorine = 6.8–7.4
d. Solvents = Substantially solvent-free
e. IR-NMR = Consistent for structure, triazole moiety intact
f. Stability = Less than 10% loss for 1 month at 56° C.

E. Sodium Levulinate

1. Dissolve 50 grams of levulinic acid in 250–300 ml. of acetone.

2. Add 10–15 grams of activated charcoal (Darco KB) and slurry for 0.5 hour.

3. Remove the carbon by filtration. Wash the carbon with 50 ml. of acetone. Add the wash to the filtrate.

4. Pass the filtrate through suitable filters to remove solids, pyrogens and bacteria. Collect the filtrate in a sterile container in a sterile area.

5. Stir the sterile filtrate rapidly. Add, over a 3–5 minute interval, 250 ml. of sterile 30% sodium 2-ethylhexanoate solution in dry isopropanol. Crystals form.

6. Slurry for 30 minutes.

7. Remove the crystals by filtration and wash with 100 ml. of sterile pyrogen-free acetone.

8. Place the acetone damp crystals in 250 ml. of sterile pyrogen-free acetone and stir for 2 minutes.

9. Pass the slurry through a sterile 200 mesh screen (or mill). Stir for 20 minutes.

10. Filter (this removes the excess sodium or free-acid 2-ethylhexanoate) and wash the crystals with 150 ml. of sterile, pyrogen-free acetone.

11. Vacuum-dry the crystals at 56° C. for 24 hours. Yield: approximately 46 grams of sodium levulinate.

PROPERTIES OF SODIUM LEVULINATE a. NMR = consistent for structure
b. % water (KF) = 0.17
c. % sodium (by ash) = 16.55 (theory = 16.6)
d. solubility = >300 mg./ml.
e. pH = 6.5–8.0.

F. Sterile 20% W/V Solution of Sodium Levulinate

1. In a suitable container add 500 ml. of sterile water.

2. Add 200 grams of sodium levulinate and q.s. to 1 liter with sterile water.

3. Add 30 grams of activated charcoal (Darco G60) and slurry for 1 hour. Remove the carbon by filtration.

4. Pass the filtrate of Step 3 through a sterile 0.22 micron Millipore filter into an appropriate sterile container or tank located in a sterile area.

5. In a sterile area, using sterile techinque, the sterile filtered solution of Step 4 is filled into appropriate sterile vials.

G. Crystalline
7-[D-α-amino-α-(p-hydroxyphenyl)acetamido]-3-
(1,2,3-triazol-5-ylthiomethyl)-3-cephem-4-carboxylic acid hydrates 7-[D-α-amino -α-(p-hydroxyphenyl)acetamido]-3-(1,2,3-triazol-5-ylthiomethyl)-3-cephem-4-carboxylic acid methanolate (Procedure A) (200 mesh; 10.0 g.) is slurried in 30–40 ml. of deionized water at ambient room temperature (20°–25° C.) to give a pH 3–4 aqueous suspension. NaOH (40%) is slowly added with rapid stirring to bring the pH to 6.3–6.7. The mixture is slurried at pH 6.3–6.7 for 2 hours. The crystals are removed by filtration, washed with water and air dried at room temperature for 24 hours to give a 75–80% weight yield of 950–1000 mcg./mg. crystals of 7-[D-α-amino-α- (p-hydroxyphenyl)acetamido]-3-(1,2,3-triazol-5-ylthiomethyl)-3-cephem-4-carboxylic acid dihydrate. IR and NMR analyses were consistent for the proposed structure and indicated that the product contained no methanol but did have a trace of propylene glycol. $H_2O$, K.F. = 6.56.

A sample of the crystalline dihydrate was air dried at 37° C. for 24 hours giving the crystalline sesquihydrate of 7-[D-α-amino-α-(p-hydroxyphenyl)acetamido]-3-(1,2,3-triazol-5-ylthiomethyl)-3-cephem-4-carboxylic acid. $H_2O$, K.F. = 4.26.

A second sample of the dihydrate was air dried at 45° C. for 24 hours to give the crystalline sesquihydrate. $H_2O$, K.F. = 5.5.

A sample of the dihydrate was air dried at 56° C. for 24 hours to give the crystalline monohydrate of 7-[D-α-amino-α-(p-hydroxyphenyl)acetamido]-3-(1,2,3-triazol-5-ylthiomethyl)-3-cephem-4-carboxylic acid. $H_2O$, K.F. = 4.38 (theoretical % $H_2O$ for monohydrate— 3.75).

A sample of the dihydrate was vacuum dried over $P_2O_5$ at room temperature for 24 hours giving the crystalline hemihydrate of 7-[D-α-amino-α-(p-hydroxyphenyl)acetamido]-3-(1,2,3-triazol-5-ylthiomethyl)-3-cephem-4-carboxylic acid. $H_2$), K.F. = 2.63 (theoretical % $H_2O$ for hemihydrate — 1.91).

A sample of the dihydrate was vacuum dried at 56° C. for 24 hours giving the crystalline hemihydrate. $H_2O$, K.F. = 1.6–2.0.

COMPARATIVE PREPARATIONS

Preparation 1

7-[D-α-amino-α-(p-hydroxyphenyl)acetamido]-3-(1,2,3-triazol-5-ylthiomethyl)-3-cephem-4-carboxylic acid amorphous monohydrate - sodium pyruvate mixture for parenteral use (Label claim is 250 mg./ml. of 7-[D-amino-α-(p-hydroxyphenyl)acetamido]-3-(1,2,3-triazol-5ylthiomethyl)-3-cephem-4-carboxylic acid activity as the monohydrate)

| Formula | |
|---|---|
| Sterile amorphous monohydrate of Procedure C, 100 mesh | * 0.250 g. of activity |
| Sterile sodium pyruvate, 100 mesh | 0.280 g. |
| Sterile sodium carbonate, 100 mesh | ** 0.005 |

* The amount of monohydrate required is calculated as follows:
Potency of monohydrate = $\frac{0.250 \text{ g.} \times 1000}{\text{in mcg./mg.}}$ —Weight in grams of
** This weight is approximate. The weight of sodium carbonate required is an about which will give a solution pH of 4.7–5.7.

The cephalosporanic acid monohydrate, sodium pyruvate and sodium carbonate are blended and filled into suitable vials and capped.

The sterile sodium pyruvate used above is prepared as follows:

1. Twenty grams of pyruvic acid is dissolved in 100 ml. of methanol.
2. The solution is passed through suitable filters to remove bacteria and pyrogens.
3. Using sterile techniques, 100 ml. of sterile, pyrogen-free, 10% sodium hydroxide in methanol (w/v) solution is added with rapid stirring over a five minute period. Crystals form.
4. The mixture is cooled to about 10°–15° C. and slurried for 0.5 hour.
5. The crystals are removed by filtration, washed with 30 ml. of cold (10°–15°) sterile methanol, 50 ml. of sterile acetone and vacuum-dried at 75° C. for 24–48 hours. Yield: 16 grams of sodium pyruvate.

PROPERTIES OF SODIUM PYRUVATE a. % $H_2O$, KF = 0.4
b. % ash as sodium = 19.92 (theory = 20.0)
c. NMR = consistent for structure, no solvents present
d. Solubility: >500 mg./ml.
e. pH range: 6.5–8.0

Preparation 2

7-[D-α-amino-α-(p-hydroxyphenyl)acetamido]-3-(1,2,3-triazol-5-ylthiomethyl)-3-cephem-4-carboxylic acid amorphous mono-hydrochloride - sodium pyruvate mixture for parenteral use (Label claim is 250 mg./ml. of 7-[D-α-amino-α-(p-hydroxyphenyl)acetamido]-3-(1,2,3-triazol-5-ylthiomethyl)-3-cephem-4-carboxylic acid activity as the mono-hydrochloride)

| Formula | |
|---|---|
| Sterile amorphous monohydrochloride of Procedure D, $D_a$, or $D_b$, 100 mesh | *0.250 g. of activity |
| Sterile sodium pyruvate, 100 mesh | 0.240 g. |
| Sterile sodium carbonate, 100 mesh | **0.028 g. |

*The amount of mono-hydrochloride required is calculated as follows:
Potency of mono-hydrochloride = $\frac{0.250 \text{ g.} \times 1000}{\text{in mcg./mg.}}$ Weight in grams of mono-hydrochloride
**This weight is approximate. The weight of sodium carbonate required is an amount which will give a solution pH of 4.7–5.7.

The cephalosporanic acid mono-hydrochloride, sodium pyruvate and sodium carbonate are blended and then filled into suitable vials and capped.

Preparation 3

7-[D-α-amino-α-(p-hydroxyphenyl)acetamido]-3-(1,2,3-triazol-5-ylthiomethyl-3-cephem-4-carboxylic acid - sodium pyruvate complex or mixture (alcohol precipitation)

1. Eight and 0.5 grams (16.6 ml.) of pyruvic acid is dissolved in 20 ml. of water.
2. Ten grams of the purified methanolate from Procedure A is added with rapid stirring over a five minute interval. A pH 1.8–2.2 solution is obtained.
3. The solution is cooled to about 10° C. and 40% sodium hydroxide is added with rapid stirring to pH 4.5–5.0 (do not allow the temperature to go above 23° C. during the titration. Do not allow the pH to go over 5.5 during the titration).
4. Pass the solution through suitable sterilizing filters to remove bacteria and pyrogens.
5. Add the sterile solution, with very rapid stirring and over a 5 minute period to a mixture of 400 ml. of sterile ethanol and 50 ml. of sterile chloroform. An amorphous precipitate forms.
6. Stir the mixture for 10 minutes.
7. The solids are removed by filtration and washed with 50 ml. of a sterile mixture prepared from 400 ml. of ethanol and 50 ml. of chloroform.
8. The solids are vacuum dried at 50°–56° C. for 24 hours.

| PROPERTIES OF ALCOHOL PRECIPITATED COMPLEX OR MIXTURE |
|---|
| a. Bio-assay = 400–425 units/mg. |
| b. % H₂O, KF = 2.75 |
| c. % ash as Sodium = 11.03 |
| d. Solubility = >500 mg./ml. |
| e. NMR: - β-lactam and triazole are intact |
|          - approximately 0.1 mole equivalent of ethanol |
|          - approximately 3 moles of pyruvate. |

Preparation 4

7-[D-α-amino-α-(p-hydroxyphenyl)acetamido]-3-(1,2,3-triazol-5-ylthiomethyl)-3-cephem-4-carboxylic acid - sodium pyruvate complex or mixture (lyophilization procedure 1. Five and 0.2 ml. (6.4 grams) of pyruvic acid is dissolved in 25 ml. of deionized water.

2. Ten grams of the purified methanolate from Procedure A is added with rapid stirring over a 5 minute interval to give a pH 1.8–2.2 solution.

3. The solution is cooled to about 10° C. and 40% sodium hydroxide is added with rapid stirring up to pH 4.5–5.0 (do not allow the temperature to go above 23° C. during the titration. Do not allow the pH to go over 5.5 during titration.).

4. Pass the solution through suitable sterilizing filters to remove bacteria and pyrogens. Steps 2, 3, 4, inclusive; shoud be completed within 4 hours.

5. Lyophilize the sterile solution for 48 hours.

6. Keep the lyophilized sterile powder at 50° C. under vacuum for 24 hours.

7. Sterilely pulverize the powder to about 100–200 mesh.

| PROPERTIES OF LYOPHILIZED COMPLEX OR MIXTURE |
|---|
| a. Bio-assay = 450–500 units/mg. |
| b. % H₂O, KF = 1.8 |
| c. % ash as sodium = 8.75 |
| d. Solubility = >500 mg./ml. |
| e. NMR: - β-lactam and triazole are intact |
|          - approximately 2.5 moles of pyruvate. |

The following examples are given in illustration of, but not in limitation of the present invention. All temperatures are in degrees centigrade.

EXAMPLE 1

7-[D-α-amino-α-(p-hydroxyphenyl)acetamido]-3-(1,2,3-triazol-5-ylthiomethyl)-3-cephem-4-carboxylic acid amorphous monohydrate - sodium levulinate mixture for parenteral use Label claim is 250 mg./ml. of 7-[D-60-amino-α-(p-hydroxyphenyl)acetamido]-3-(1,2,3-triazol-5-ylthiomethyl)-3-cephem-4-carboxylic acid activity as the monohydrate)

| | Formula |
|---|---|
| Sterile amorphous monohydrate of Procedure C, 200 mesh | * 0.250 g. of activity |
| Sterile sodium levulinate, 200 mesh | 0.210 g. |

The amount of monohydrate required for 250 mg./ml. activity is calculated as follows:

$$\frac{0.250 \text{ grams} \times 1000}{\text{Potency of monohydrate in mcg./mg.}} = \text{Weight in grams of monohydrate}$$

The cephalosporanic acid monohydrate and sodium levulinate are blended, passed through a suitable mill containing the equivalent of a 60 mesh screen and blended again. The blend is then filled into suitable vials and capped.

The sodium levulinate used above may be replaced by calcium levulinate or potassium levulinate to give equivalent physical mixtures.

EXAMPLE 2

7-[D-α-amino-α-(p-hydroxyphenyl)acetamido]-3-(1,2,3-triazol-5-ylthiomethyl)-3-cephem-4-carboxylic acid - sodium levulinate complex (or mixture) (lyophilization process)

A mixture of 1 gram of sterile 7-[D-α-amino-α-(p-hydroxyphenyl)acetamido]-3-(1,2,3-triazol-5-ylthiomethyl)-3-cephem-4-carboxylic acid amorphous monohydrate and 0.80–0.85 grams of sterile sodium levulinate is dissolved in 2.5–3.0 ml. of water. The aqueous solution is sterilely lyophilized for 16–24 hours to give the desired water-soluble complex or mixture.

EXAMPLE 3

7-[D-α-amino-α-(p-hydroxyphenyl)acetamido]-3-(1,2,3-triazol-5-ylthiomethyl)-3-cephem-4-carboxylic acid - sodium levulinate complex (or mixture) (alcohol precipitation process)

A mixture of 1 gram of sterile 7-[D-α-amino-α-(p-hydroxyphenyl)acetamido]-3-(1,2,3-triazol-5-ylthiomethyl)-3-cephem-4-carboxylic acid amorphous monohydrate and 0.80–0.85 grams of sterile sodium levulinate is dissolved in 2.5–3.0 ml. of water. The aqueous solution is added with rapid stirring to 15–20 volumes of sterile isopropanol (n-propanol or ethanol may also be used) to precipitate the solid composition. The precipitate is filtered, washed with isopropanol and acetone and dried in a vacuum oven at 56° C. for 24 hours.

EXAMPLE 4

7-[D-α-amino-α-(p-hydroxyphenyl)acetamido]-3-(1,2,3-triazol-5-ylthiomethyl)-3-cephem-4-carboxylic acid amorphous mono-hydrochloride - aqueous sodium levulinate vehicle combination One million units (approximately 1.1 g.) of 200 mesh sterile, pyrogen-free 7-[D-α-amino-α-(p-hydroxyphenyl)acetamido]-3-(1,2,3-triazol-5-ylthiomethyl-3-cephem-4-carboxylic acid amorphous mono-hydrochloride is placed in a suitable capped sterile vial. To the vial is added 3.2 ml. of a sterile aqueous solution containing 0.83 grams of sodium levulinate. The vial is shaken well to produce 4 ml. of a pH 4.5–6.5 solution having 250 mg./ml. of 7-[D-αamino-α-(p-hydroxyphenyl)acetamido]-3-(1,2,3-triazol-5-ylthiomethyl)-3-cephem-4-carboxylic acid activity. This solution may be used parenterally as is or diluted to any lower concentration desired.

EXAMPLE 5

The general procedure of Example 3 is repeated using an aqueous solution comprised of 0.56 g. of amorphous monohydrate and 0.420 g. of sodium levulinate in 3.2 ml. water. The solution is slowly added to 20 volumes of 1-propanol to produce a white precipitate. The precipitate is filtered, washed with 1-propanol and several volumes of acetone and dried in a vacuum oven at 56° C. for 24 hours. Yield = 0.460 g. (46.9%). Bio-assay = 665 mcg./mg. A sample dissolved in $D_2O$ and analyzed by NMR showed no 1-propanol and about 1.5 moles of levulinate.

EXAMPLE 6

The general procedure of Example 2 is repeated using an aqueous solution comprising 0.660 g. of crystalline cephalosporanic acid sesquihydrate, 0.495 g. of sodium levulinate and 1.39 g. of water. The aqueous solution is lyophilized for 16–24 to give the desired solid composition.

K.F. ($H_2O$) = 1.22%
% Na (ash) = 4.15%

Physical And Biological Data

A. Stability of Aqueous Solutions of Amorphous Monohydrate and Sodium Levulinate Mixture at Room Temperature

| Initial Activity in mg./ml. | % Loss in Activity Hours | | | | | |
|---|---|---|---|---|---|---|
| | 1 | 2 | 3 | 4 | 6 | 8 |
| 250 | 0 | 4 | 2 | 5 | 6 | — |
| 25 | — | 1.9 | — | 0 | 1.9 | 0 |
| 10.5 | — | 0 | — | 0 | 0 | 0–3 |

Aqueous solutions (250 mg./ml.) of the amorphous mono-hydrochloride and sodium levulinate appeared stable for 24 hours (no loss) at room temperature. At 25 mg./ml. under 10% loss was noted for 3 days at room temperature.

B. Blood Levels in Mice After Intramuscular Administration of *10 mg./kg.

| | Antibiotic Concentration (μg/ml.) | | | |
|---|---|---|---|---|
| | 0.25 | 0.5 | 1 | 1.5 |
| Formulation | Hours After Administration | | | |
| Cephalosporin 1,2-propylene glycolate | 18.9 | 17.4 | 12.3 | 9.0 |
| Cephalosporin Monohydrate - Sodium Levulinate Mixture | 17.1 | 14.3 | 9.7 | 6.7 |
| Cephalosporin Monohydrate - Sodium Levulinate Alcohol Precipitated Composition | 17.8 | 15.9 | 11.3 | 8.8 |

*The dose was in terms of the cephalosporin mono-hydrate.

C. Blood Levels in Mice After Oral Administration of *100 mg./kg.

| | Antibiotic Concentration (μg/ml.) | | | |
|---|---|---|---|---|
| | 9.5 | 1 | 2 | 3.5 |
| Formulation | Hours After Administration | | | |
| Cephalosporin 1,2-Propylene glycolate | 45.8 | 44.7 | 26.6 | 9.7 |
| Cephalosporin Monohydrate - Sodium Levulinate Mixture | 49.2 | 45.2 | 23.2 | 8.5 |
| Cephalosporin Monohydrate - Sodium Levulinate Alcohol Precipitated | 34.1 | 33.3 | 22.3 | 9.6 |

*The dose was in terms of the cephalosporin monohydrate.

D. Minimum Inhibitory Concentrations

Samples of each of the products indicated below after solution in water and dilution with Nutrient Broth were found to exhibit the following Minimum Inhibitory Concentrations (M.I.C.) in mcg./ml. versus the indicated microorganisms as determined by overnight incubation at 37° C. by tube dilution.

| Organism | | M.I.C. in mcg./ml. | | | | |
|---|---|---|---|---|---|---|
| | | Composition of Ex. 1 | Composition of Ex. 3 | +Cephalosporin 1,2-Propylene Glycolate | Cephalothin | Cephalexin |
| D. pneumoniae +5% serum* | A9585 | 0.13 | 0.13 | 0.13 | 0.13 | 1 |
| Str. pyogenes +5% serum* | A9604 | .016 | 0.016 | .03 | .06 | 0.5 |
| S. aureus Smith** | A9537 | 0.25 | 0.25 | 0.25 | 0.13 | 1 |
| S. aureus Smith** +50% serum | A9537 | 2 | 2 | 2 | 0.5 | 2 |
| S. aureus BX1633-2 at $10^{-3}$ dil'n | A9606 | 0.5 | 0.5 | 0.5 | 0.25 | 2 |
| S. aureus BX1633-2 at $10^{-2}$ dil'n | A9606 | 2 | 2 | 2 | 0.25 | 4 |
| 7-[S. aureus meth.-resist.; at $10^{-3}$ dil'n | A15097 (37° C) (28° C) | 4 | 2 4 | 2 4 | 4 4 | 16 32 |

-continued

| Organism | | M.I.C. in mcg./ml. | | +Cephalosporin 1,2-Propylene Glycolate | Cephalothin | Cephalexin |
|---|---|---|---|---|---|---|
| | | Composition of Ex. 1 | Composition of Ex. 3 | | | |
| Sal. enteritidis | A9531 | 0.5 | 0.25 | 0.5 | .06 | 4 |
| E. coli Juhl | A15119 | 1 | 1 | 1 | 8 | 8 |
| E. coli | A9675 | 4 | 2 | 4 | 32 | 16 |
| K. pneumoniae | A9977 | 0.5 | 0.5 | 1 | 2 | 4 |
| K. pneumoniae | A15130 | 2 | 2 | 2 | 16 | 8 |
| Pr. mirabilis | A9900 | 0.5 | 0.5 | 0.5 | 1 | 4 |
| Pr. morganii | A15153 | 16 | 16 | 32 | >125 | >125 |
| Ps. aeruginosa | A9843A | >125 | >125 | >125 | >125 | >125 |
| Ser. marcescens | A20019 | 125 | >125 | >125 | >125 | >125 |
| Ent. cloacae | A9656 | >125 | >125 | >125 | >125 | >125 |
| Ent. cloacae | A9657 | 0.5 | 1 | 1 | 2 | 4 |
| Ent. cloacae | A9659 | 16 | 32 | 32 | >125 | >125 |

*50% Nutrient Broth – 45% Antibiotic Assay Broth
**at $10^{-4}$ dilution
+7-[D-$\alpha$-amino-$\alpha$-(p-hydroxyphenyl)acetamido]-3-(1,2,3-triazol-5-ylthiomethyl)-3-cephem-4-carboxylic acid.

E. Comparative Nephrotoxicity of Water-Soluble Compositions in Rabbits

Method

The nephrotoxic potentials of several water-soluble forms of 7-[D-$\alpha$-amino-$\alpha$-(p-hydroxyphenyl)acetamido]-3-(1,2,3-triazol-5-ylthiomethyl)-3-cephem-4-carboxylic acid were investigated in male New Zealand White rabbits according to the following design:

| Group No. | Test Material | *Drug Conc. (mg./ml.) | *Single Dose (mg./kg.) | Vol. of Injection (ml./kg.) | No. of Rabbits |
|---|---|---|---|---|---|
| I | Sodium Pyruvate Composition of Comparative Preparation 3 | 10.0 | 100 | 1.0 | 4 |
| II | Monohydrate-Sodium Pyruvate Mixture of Comparative Preparation 1 | 10.0 | 100 | 1.0 | 4 |
| III | Monohydrate-Sodium Levulinate Mixture of Example 1 | 10.0 | 100 | 1.0 | 4 |
| IV | Sterile Water | — | — | 1.0 | 4 |

The test materials were given by single intravenous administration into a lateral ear vein at an injection speed of 2 minutes/dose. Forty-eight hours after dosing, the animals were sacrificed and gross and microscopic examinations of the kidneys were performed.

| Results | | | **Microscopic | |
|---|---|---|---|---|
| *Compound And Dose | Rabbit No. | **Gross Changes | Nephrotoxicity | Average Group Rating |
| Sodium Pyruvate Composition of Comparative Preparation 3 | 1 | 3 | 3 | |
| | 2 | 2 | 3 | |
| | 3 | 1 | 2 | 3.0 |
| | 4 | 3 | 4 | |
| Monohydrate - Sodium Pyruvate Mixture of Comparative Preparation 1 | 5 | ± | 1 | |
| | 6 | ± | 1 | |
| | 7 | 2 | 2 | 1.5 |
| | 8 | 2 | 2 | |
| Monohydrate - Sodium Levulinate Mixture of Example 1 | 9 | 0 | 0 | |
| | 10 | 1 | 2 | |
| | 11 | 0 | 0 | 0.75 |
| | 12 | ± | 1 | |
| Control (Sterile Water) 1 ml./kg. | 13 | 0 | 0 | |
| | 14 | 0 | 0 | |
| | 15 | 0 | 0 | 0 |
| | 16 | 0 | 0 | |

*In terms of 7-[D-$\alpha$-amino-$\alpha$-(p-hydroxyphenyl)acetamido]-3-(1,2,3-triazol-5-ylthiomethyl)-3-cephem-4-carboxylic acid activity.
**0 = not remarkable  2 = mild
± = questionable  3 = moderate
1 = minimal  4 = severe

We claim:

1. A stable, solid, water-soluble antibiotic composition for reconstitution upon addition of sterile water as a stable injectable solution of 7-[D-$\alpha$-amino-$\alpha$-(p-hydroxyphenyl)acetamido]-3-(1,2,3-triazol-5-ylthiomethyl)-3-cephem-4-carboxylic acid, said composition comprising a mixture of one part by weight of 7-[D-$\alpha$-amino-$\alpha$-(p-hydroxyphenyl)acetamido]-3-(1,2,3-triazol-5-ylthiomethyl)-3-cephem-4-carboxylic acid hydrate and about 0.25 to about 2.0 parts by weight of sodium, potassium or calcium levulinate.

2. The composition of claim 1 wherein the 7-[D-$\alpha$-amino-$\alpha$-(p-hydroxyphenyl)acetamido]-3-(1,2,3-triazol-5-ylthiomethyl)-3-cephem-4-carboxylic acid hydrate is the amorphous monohydrate.

3. The composition of claim 2 wherein the levulinic acid salt is sodium levulinate.

4. The composition of claim 3 suitable upon reconstitution with sterile water as a stable pH 4.5 to 7.8 injectable solution of 7-[D-$\alpha$-amino-$\alpha$(p-hydroxyphenyl)acetamido]-3-(1,2,3-triazol-5-ylthiomethyl)-3-cephem-4-carboxylic acid, said composition comprising a mixture of one part by weight of amorphous cephalosporanic acid monohydrate and about 0.75 to 1.0 parts by weight of sodium levulinate.

5. The stable injectable preparation of 7-[D-α-amino-α-(p-hydroxyphenyl)acetamido]-3-(1,2,3-triazol-5-ylthiomethyl)-3-cephem-4-carboxylic acid, said preparation comprising in aqueous solution one part by weight of 7-[D-α-amino-α-(p-hydroxyphenyl)acetamido]-3-(1,2,3-triazol-5-ylthiomethyl-3-cephem-4-carboxylic acid hydrate or hydrochloride and about 0.25 to about 2.0 parts by weight of sodium, potassium or calcium levulinate and having a pH in the range of 3.5 to 8.0.

6. The preparation of claim 5 wherein the cephalosporanic acid compound is the amorphous monohydrate or amorphous mono-hydrochloride.

7. The preparation of claim 6 wherein the levulinic acid salt is sodium levulinate.

8. The preparation of claim 7 wherein the cephalosporanic acid compound and levulinate are employed in a ratio of about 1:0.75–1.0, respectively, to give a pH 4.5 to 7.8 solution.

9. The preparation of claim 8 wherein the concentration of 7-[D-α-amino-α-(p-hydroxyphenyl)acetamido]-3-(1,2,3-triazol-5-ylthiomethyl)-3-cephem-4-carboxylic acid is provided in solution is from about 10 to 350 mg./ml. of solution.

10. The preparation of claim 9 wherein the cephalosporanic acid compound is 200 mesh amorphous monohydrate.

11. A process for the preparation of a stable, solid, water-soluble composition suitable upon reconstitution with sterile water as a stable injectable solution of 7-[D-αamino-α-(p-hydroxyphenyl)acetamido]-3-(1,2,3-triazol-5-ylthiomethyl)-3-cephem-4-carboxylic acid; which process comprises
  1. forming an aqueous solution of one part by weight of 7-[D-α-amino-α-(p-hydroxyphenyl)acetamido]-3-(1,2,3-triazol-5-ylthiomethyl)-3-cephem-4-carboxylic acid hydrate or hydrochloride and about 0.25 to about 2.0 parts by weight of sodium, potassium or calcium levulinate; and
  2. lyophilizing the so-produced aqueous solution to produce the desired solid composition.

12. The process of claim 11 wherein the cephalosporanic acid compound is the amorphous monohydrate or amorphous mono-hydrochloride.

13. The process of claim 12 wherein the levulinic acid salt is sodium levulinate.

14. The process of claim 13 wherein the cephalosporanic acid compound and sodium levulinate are employed in a proportion of about 1:0.75–1.0, respectively.

15. The process of claim 14 wherein the aqueous solution of step (1) comprises about one gram of cephalosporanic acid compound and about 0.8 to 0.85 grams of sodium levulinate per 2.5 to 3.0 ml. of water.

16. A process for the preparation of a stable, solid, water-soluble composition suitable upon reconstitution with sterile water as a stable injectable solution of 7-[D-α-amino-α-(p-hydroxyphenyl)acetamido]-3-(1,2,3-triazol-5-ylthiomethyl)-3-cephem-4-carboxylic acid; which process comprises
  1. forming an aqueous solution of one part by weight of 7-[D-α-amino-α-(p-hydroxyphenyl)acetamido]-3-(1,2,3-triazol-5-ylthiomethyl)-3-cephem-4-carboxylic acid hydrate or hydrochloride and about 0.25 to about 2.0 parts by weight of sodium, potassium or calcium levulinate; and
  2. adding the so-produced aqueous solution to a sufficient quantity of ethanol, n-propanol or isopropanol to effect precipitation of the desired solid composition.

17. The process of claim 16 wherein the cephalosporanic acid compound is the amorphous monohydrate or amorphous mono-hydrochloride.

18. The process of claim 17 wherein the levulinic acid salt is sodium levulinate.

19. The process of claim 18 wherein the cephalosporanic acid compound and sodium levulinate are employed in a proportion of about 1:0.75–1.0, respectively.

20. The process of claim 19 wherein the aqueous solution of Step (1) comprises about one gram of cephalosporanic acid compound and about 0.8 to 0.85 grams of sodium levulinate per 2.5 to 3.0 ml. of water.

21. The process of claim 20 wherein the aqueous solution of Step (1) is added with rapid stirring to about 15 to 20 volumes of the ethanol, n-propanol or isopropanol.

* * * * *